United States Patent [19]

van Andel

[11] Patent Number: Plant 6,193

[45] Date of Patent: May 31, 1988

[54] ALSTROEMERIA VARIETY 'STALBEL'

[75] Inventor: Jacob van Andel, Aalsmeer, Netherlands

[73] Assignee: Von Staaveren B.V., Aalsmeer, Netherlands

[21] Appl. No.: 872,869

[22] Filed: Jun. 11, 1986

[51] Int. Cl.[4] ..... A01H 5/00

[52] U.S. Cl. ..... Plt./68

[58] Field of Search ..... Plt./68

*Primary Examiner*—James R. Feyrer

*Attorney, Agent, or Firm*—Charles W. Rummler; W. Dennis Drehkoff

[57] ABSTRACT

A new variety of Alstroemeria characterized by its very large blooms, the outer petals of which are distinguished by a mainly white coloration and having short, parallel streaks of a purplish color at each side of a short groove at the petal tip, the inner petals being more narrow in form and being mainly of a yellow coloration with the petal tips being white at their outer ends with a purplish blotch at the tip, the inner petals being further marked with short, deep purplish pencil stripes which spread outwardly from the base of the petals to the petal tips. This plant is further distinguished by its strong, vigorous and upright growth habit with the main stem reaching a height of about 180 cm., each stem bearing a raceme of many flowers at its upper portion and the flowers being produced profusely and continuously from spring through fall.

1 Drawing Sheet

BACKGROUND OF THE NEW PLANT

This new Alstroemeria plant originated as a seedling resulting from my crossing of plants selected from individually identified members of my breeding stock maintained at Aalsmeer, The Netherlands, for breeding purposes, this particular seedling having been selected by me for propagation and test because of the very large size of its generally white flowers which appeared to be produced profusely on strong, upright stems from a generally umbel formation. This new plant has resulted from breeding efforts carried on by me at Aalsmeer since 1982 with the object of producing new types of Alstroemeria hybrids having new and unusual coloration. This particular seedling was selected by me for propagation and test beause of the very large size and generally white coloration of its blooms, the propagation being done by means of rhizomes with very satisfactory results which prompted me to direct further propagation of this new plant by dividing rhizomes of several successive generations, which demonstrated that the novel and distinctive characteristics of this new variety would hold true from generation to generation and appeared to be firmly fixed for continued asexual propagation.

DESCRIPTION OF THE DRAWING

This new Alstroemeria hybrid is illustrated by the accompanying photographic drawing which, in full color, shows flowers of a blooming umbel of the plant and demonstrates the unique and distinctive coloration and form of the flowers, the color rendition being as nearly true as is possible to obtain by conventional photographic procedures.

DESCRIPTION OF THE NEW PLANT

The following is a detailed description of my new Alstroemeria hybrid as observed at Aalsmeer, The Netherlands, the color designations being according to The R.H.S. Colour Chart of The Royal Horticultural Society of London, England.

THE PLANT

Origin: Seedling.

Parentage:

*Seed parent.*—Breeding Stock Plant No. 1533-6.

*Pollen parent.*—Breeding Stock Plant No. 0441-2.

These parent plants are individually identified by their respective numbers in my breeding records maintained at my offices at Aalsmeer.

Classification: Alstroemeria Hybrid.

Form: Erect and tall bush.

Height: About 180 cm.

Main stem:

Length.—About 180 cm. with flower bearing branches in simple umbel arrangement at its top.

Growth: Strong, vigorous and upright.

Foliage:

*Quantity.*—Abundant.

*Number of leaves.*—Varying with the season.

*Size of leaf.*—Large.

*Leaf shape.*—Generally elliptic with entire margins.

*Color.*—Upper side — Middle Green. Under side — Grey Green.

Rhizomes:

*Color.*—White.

*Size.*—Varying with age of plant.

THE BUD

Form: Pear shaped.

Size: Normal.

*Diameter.*—About 2 cm.

*Length.*—About 4 cm.

*Calyx.*—This plant has no calyx, the six petals of the flower being perianth and dividing simultaneously.

Peduncle:

*Length.*—Up to about 16 cm.

*Character.*—Erect.

*Color.*—Green.

THE FLOWER

Blooming habit: Continuous and profusely from spring through fall.

Flower size: Very large.

*Diameter.*—About 6.5 to 7 cm.

*Depth.*—About 6 cm.

Borne: Singly.

Shape: Funnel-like with petal tips tending to curve outwardly.

Petalage:

*Number of petals.*—Six.

*Arrangement.*—Two concentric circles of three petals each.

*Form.*—Outer petals — Obovate with emarginate tip and undulate margins. Inner petals — Generally ovate with acute tip and entire margins.

*Texture.*—Soft.

*Appearance.*—Satiny.

*Color.*—Outer petal: Body, White, 155C, with 56B at the base and with short, narrow blotches of 56B at each side of the groove at the petal apex. Inner petal: The body is generally Yellow, 12A, with white tip portion and having numerous short pencil stripes extending outwardly from the base to the tip margins. Reverse side, 12B. The reverse side of the outer petal is 56C.

Peduncle:

*Length.*—About 2 cm.

*Character.*—Strong.

*Color.*—Light Green.

Persistence: The flowers hang on and dry.

Fragrance: None.

Lasting quality:

*On plant.*—About 20 days.

*As a cut flower.*—About 14 days.

REPRODUCTIVE ORGANS

Stamens:

*Number.*—Six.

*Arrangement.*—Normal.

*Size.*—About 8 cm.

*Color.*—Grey Green.

Filaments:

*Length.*—About 35 mm.

*Color.*—White at base, pink at top.

Pollen:

*Color.*—Yellow.

Pistils:

*Number.*—One.

Styles:

*Length.*—About 3 mm.

*Color.*—White at base, pink at top.

Stigma:

*Color.*—Violet.

I claim:

1. A new and distinctive Alstroemeria hybrid, substantially as herein shown and described, characterized by its very large blossoms having large and generally ovate white outer petals each of which is marked by a pair of dark streaks at the petal apex and the inner petals being long, elliptic form with the main portion of the petal body being yellow and the tip portions being white with the entire body of the petal being marked with numerous short pencil stripes extending outwardly from the base of the petal to all of its margins.

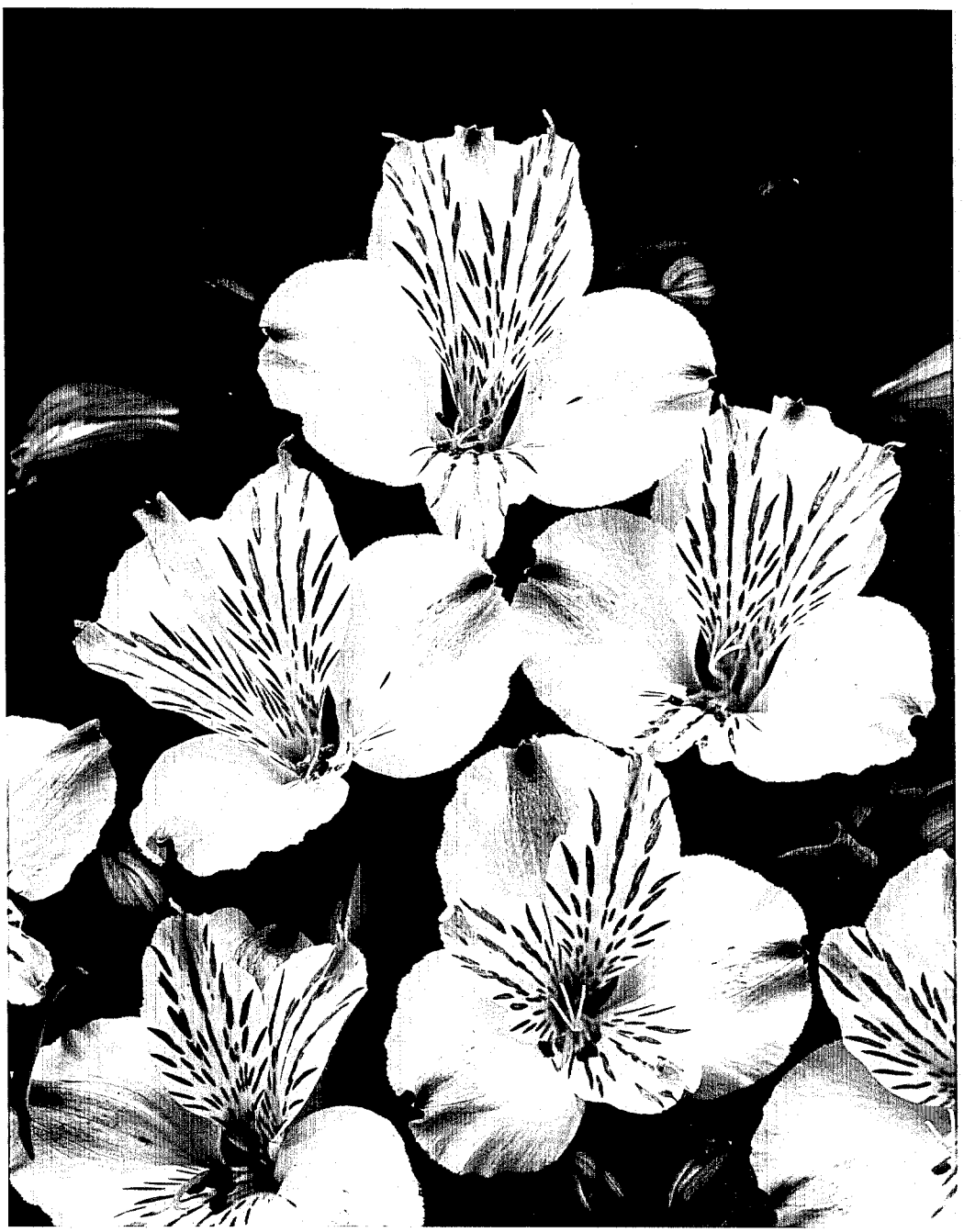

* * * * *